(12) United States Patent
Griswold

(10) Patent No.: US 8,465,436 B2
(45) Date of Patent: Jun. 18, 2013

(54) ENDOLUMINAL IMPLANT WITH LOCKING AND CENTERING FIXATION SYSTEM

(75) Inventor: Erik Griswold, Penngrove, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 383 days.

(21) Appl. No.: 12/768,235

(22) Filed: Apr. 27, 2010

(65) Prior Publication Data

US 2011/0264194 A1  Oct. 27, 2011

(51) Int. Cl.
*A61B 5/021* (2006.01)
*A61F 2/90* (2006.01)
*A61F 2/82* (2006.01)
*A61F 2/88* (2006.01)

(52) U.S. Cl.
USPC ........... 600/486; 600/481; 600/485; 606/108; 606/200; 623/1.11; 623/1.12; 623/1.13; 623/1.14; 623/1.15; 623/1.16; 623/1.17; 623/1.2; 623/1.21; 623/1.22; 623/1.23; 623/1.36

(58) Field of Classification Search
USPC ................. 600/300, 354, 481, 485, 486, 500, 600/504–507; 606/108, 200; 623/1.11–1.17, 623/1.2–1.23, 1.36
See application file for complete search history.

(56) References Cited

U.S. PATENT DOCUMENTS

| | | | |
|---|---|---|---|
| 6,416,474 B1 | 7/2002 | Penner et al. | |
| 6,635,070 B2 | 10/2003 | Leeflang et al. | |
| 7,181,261 B2 | 2/2007 | Silver et al. | |
| 7,572,228 B2 | 8/2009 | Wolinsky et al. | |
| 7,621,870 B2 * | 11/2009 | Berrada et al. | 600/200 |
| 8,057,399 B2 * | 11/2011 | Greenland et al. | 600/488 |
| 2002/0188207 A1 * | 12/2002 | Richter | 600/486 |
| 2005/0154321 A1 | 7/2005 | Wolinsky et al. | |
| 2005/0277977 A1 | 12/2005 | Thornton | |
| 2006/0200030 A1 | 9/2006 | White et al. | |
| 2008/0071178 A1 * | 3/2008 | Greenland et al. | 600/486 |
| 2009/0254138 A1 * | 10/2009 | Stahmann | 607/6 |

* cited by examiner

*Primary Examiner* — Patricia Mallari
*Assistant Examiner* — Puya Agahi

(57) ABSTRACT

An implant centering system includes a sensor connected to a hollow cylindrical anchor via at least two struts. The hollow cylindrical anchor is transformable between a radially compressed configuration for delivery and a radially expanded configuration for lodging against a vessel wall. The struts longitudinally relocate the sensor between a first position in which the sensor is longitudinally spaced apart from the radially compressed anchor, and a second position in which the sensor is at least partially within a lumen of the radially expanded anchor and radially centered within vessel. In one embodiment, the struts are heat-set into a curved configuration and an externally applied force longitudinally relocates the sensor until the struts lock over center into their heat-set configuration. In another embodiment, radial expansion of the anchor longitudinally relocates the sensor without an externally applied force.

11 Claims, 5 Drawing Sheets

ENDOLUMINAL IMPLANT WITH LOCKING AND CENTERING FIXATION SYSTEM

FIELD OF THE INVENTION

The invention relates to a medical device for endoluminal implantation within a patient's vessel. A fixation system is provided for centering and locking the implant within the vessel. The medical device may be a leadless sensor.

BACKGROUND OF THE INVENTION

Medical implants such as leadless sensors or other apparatuses may be delivered via catheter and implanted within a vessel or vasculature. In cases where the target site for implantation is reached through an extended and sometimes tortuous route, the implant preferably has, or can be temporarily compacted to have a small delivery profile or configuration. One major vessel of interest for locating a leadless sensor is the main pulmonary artery and its branches. The right pulmonary artery is a particularly challenging location in which to endoluminally deliver a leadless sensor or other apparatus because navigation of the multiple 180° bends to reach the right pulmonary artery from a femoral vein access site is very difficult. Specifically, one exemplary vascular path includes inserting a delivery catheter into a femoral vein, tracking the catheter to the inferior vena cava, into the right atrium, through the tricuspid valve into the right ventricle, and through the pulmonary valve to access the pulmonary trunk, then selectively entering the right pulmonary artery.

Once the delivery device reaches the target implantation site, a reliable means of fixation must be deployed to secure the sensor within the vessel. It is desirable to secure the sensor radially centered within the vessel, with little or no contact with the vessel wall, in order to avoid tissue ingrowth and obtain accurate sensor measurements. Particularly within blood vessels, the sensor is subjected to a continuous pulsatile fluid flow. The potential of detachment of a sensor from the implantation site represents a serious and possibly life-threatening event. Thus, secure fixation of leadless implants is important for successful operation of the implant as well as safety of the patient.

Accordingly, it is an object of the present invention to provide a fixation device or system that has a minimized delivery profile and that deploys to secure a sensor radially centered within the vessel.

BRIEF SUMMARY OF THE INVENTION

Embodiments hereof relate to a medical implant including a sensor connected to a hollow cylindrical anchoring component, hereinafter referred to as an anchor. The anchor is transformable between a radially compressed configuration for delivery within a vasculature and a radially expanded configuration for lodging against a vessel wall. At least two struts each have a first end attached to the sensor and a second end attached to the anchor. The struts may operate to longitudinally relocate the sensor between a first position in which the sensor is longitudinally spaced apart from the radially compressed anchor, and a second position in which at least a portion of the sensor is located and centered within a lumen of the radially expanded anchor. In one embodiment, the struts are locked in an over-center configuration wherein the first ends of the struts longitudinally have passed the second ends of the struts.

In an embodiment, a method of radially centering a sensor within a vessel includes percutaneously introducing an implant comprising a sensor that is connected to a hollow cylindrical anchor by at least two struts. In an initial delivery configuration, the sensor is longitudinally spaced apart from the anchor. The implant is advanced through the vasculature to an implantation site, and the anchor is radially expanded to lodge against a vessel wall at the implantation site. A force is then applied to transform the implant into a deployed configuration by longitudinally relocating the sensor to a position in which at least a portion of the sensor is located and centered within a lumen of the radially expanded anchor. The struts are locked in an over-center configuration.

Another method of radially centering a sensor within a vessel includes percutaneously introducing an implant comprising a sensor that is spaced apart from and connected to a hollow cylindrical anchor via at least two struts. The sensor is advanced through the vasculature to an implantation site, and the anchor is radially expanded to lodge against a vessel wall at the implantation site. The action of radially expanding anchor longitudinally relocates the sensor via the struts to a position in which at least a portion of the sensor is located and centered within a lumen of the radially expanded anchor.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

DETAILED DESCRIPTION OF THE INVENTION

Figure 1:
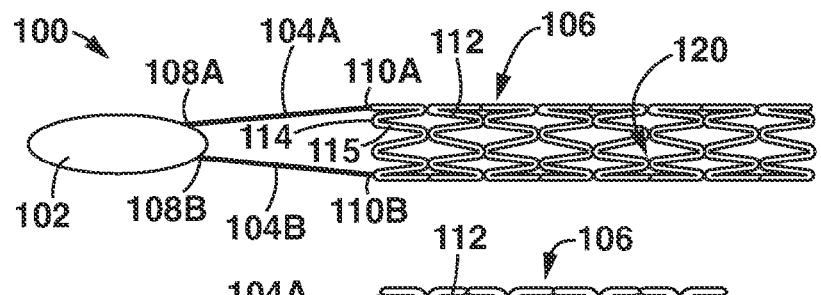
FIG. 1 is a side view of an embodiment of an implant in accordance with the invention, shown in a delivery configuration in which a sensor is longitudinally separated from a compressed anchor.

Specific embodiments of the present invention are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician.

The following detailed description is merely exemplary in nature and is not intended to limit the invention or the application and uses of the invention. Although the description of the invention is in the context of treatment of blood vessels such as the coronary, carotid and renal arteries, the invention may also be used in any other body passageways where it is deemed useful. Furthermore, there is no intention to be bound by any expressed or implied theory presented in the preceding technical field, background, brief summary or the following detailed description.

Embodiments hereof relate to an implant 100 including a leadless sensor 102 and a fixation system for locking and radially centering the sensor within vasculature such as a blood vessel. Implant 100 comprises an anchor 106 for radially centering and securing a leadless sensor 102 in a vessel. In one embodiment, sensor 102 is an active leadless pressure sensor. An exemplary leadless sensor that may be adapted for use in embodiments hereof is of the type described U.S. Pat. No. 7,572,228 to Wolinsky et al. An active leadless pressure sensor system implanted within the body may be designed to continuously monitor blood pressure, allowing physicians to proactively administer medications so that patients avoid dangerous blood pressure spikes. For purposes of describing the invention hereof only the basic structure of sensor 102 is described herein. Generally, sensor 102 has a capsule-shaped housing that hermetically encloses the sensor's electrical components, including a wireless communication system and an internal power source. The sensors described herein are sized to be delivered endoluminally within delivery systems hereof tracked through the vasculature from a percutaneous entry site such as a femoral, jugular or subclavian vein or artery, and may have an outer diameter between 16-18 French (5.3-6 mm). In accordance with embodiments hereof, the sensor 102 described herein may be delivered through the vasculature to be implanted in either the left or right pulmonary artery. In other embodiments, medical implants described herein may be implanted within other blood vessels such as the aorta, renal arteries, or inferior or superior vena cava. Although medical implants described herein are described as leadless pressure sensors, in other embodiments hereof delivery and fixation systems and methods herein may be used to deliver and implant other medical devices that are configured to be secured within blood vessels, such as another type of sensor device or a stimulator device, which may or may not be "leadless" or self-contained.

Sensor 102 is connected to an anchor 106 via at least struts 104A, 104B. As will be explained in more detail below, anchor 106 is a radially-expandable hollow cylindrical structure that is configured to lodge against a vessel wall when expanded in situ. Struts 104A, 104B have first ends 108A, 108B, respectively, connected to a distal end of sensor 102 and second ends 110A, 110B, respectively, connected to a proximal end of anchor 106. Although not required, in one embodiment, second ends 110A, 110B of struts 104A, 104B are positioned at diametrically opposite locations on the proximal end circumference of anchor 106. Although shown with only two struts 104A, 104B connecting sensor 102 to anchor 106, it will be apparent to those of ordinary skill in the art that implant centering fixation implant 100 may include three or more struts that may be attached at equally-spaced locations on the proximal end circumference of anchor 106. Struts 104A, 104B operate to longitudinally relocate sensor 102 between an initial or delivery configuration shown in FIG. 1 in which sensor 102 is longitudinally spaced apart from radially compressed anchor 106 and a final or deployed configuration in which sensor 102 is at least partially located within a lumen of radially expanded anchor 106 shown in FIG. 5. As will be explained in more detail herein, in operation, struts 104A, 104B lock into an over-center position curved radially inward from their attachment points on anchor 106 to hold at least a distal portion of sensor 102 centered and located within the lumen 120 of expanded anchor 106.

In order to percutaneously deliver and track implant 100 through a patient's vasculature, anchor 106 is radially compressed and struts 104A, 104B are generally straight to longitudinally separate or space sensor 102 apart from anchor 106 as shown in the implant delivery configuration of FIG. 1. Longitudinally separating sensor 102 from anchor 106, rather than locating sensor 102 within the lumen 120 of anchor 106 during delivery minimizes the profile of the delivery system. FIGS. 1-5 illustrate implant 100 being transformed from the initial or delivery configuration in which sensor 102 is longitudinally separated from compressed anchor 106 to the final or deployed configuration in which at least a distal portion of sensor 102 is centered and locked within the lumen 120 of expanded anchor 106.

Figure 2:
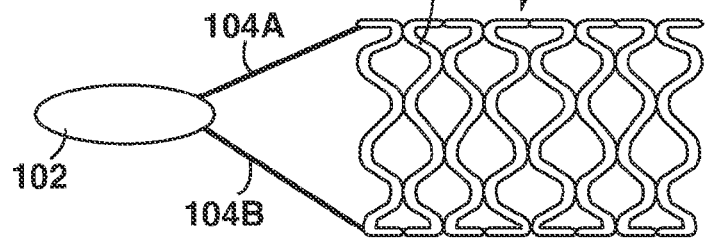
FIG. 2 is a side view of the implant of FIG. 1, wherein the anchor is expanded.

Referring to FIGS. 1 and 2, radial expansion of anchor 106 is the first step of deploying implant 100. Anchor 106 is a generally tubular or cylindrical stent-like structure having a lumen 120 therethrough and being transformable between the radially compressed configuration of FIG. 1 for transluminal catheter delivery within a vasculature and the radially expanded configuration of FIG. 2 for lodging against a vessel wall. In one embodiment, a plurality of radially compressible rings 112 is joined in series to form the cylindrical tubular body of anchor 106. One of ordinary skill in the art will appreciate that anchor 106 can have any number of rings 112 depending upon the desired length of anchor 106. For example when the target implantation site is relatively short, it would be desirable for anchor 106 to have a small number of rings such as between two and four rings. Rings 112 may have any suitable configuration, such as a zig-zag or sinusoidal wireform pattern of straight segments 115 with crowns 114 (i.e., alternating crowns facing opposite longitudinal directions) connecting adjacent straight segments 115. After being radially crimped or otherwise compressed for delivery to a target site within a vessel, anchor 106 may radially self-expand or may be radially expanded via inflation of a balloon (not shown) such that anchor 106 securely engages the vessel wall. Those of ordinary skill in the art would recognize that anchor 106 may adapted from other known stent-like configurations. For example, and not by way of limitation, the anchor may be selected from self-expanding and balloon-expandable stents such as those shown and described in U.S. Pat. No. 4,733,665 to Palmaz, U.S. Pat. No. 4,800,882 to Gianturco, U.S. Pat. No. 4,886,062 to Wiktor, U.S. Pat. No. 5,133,732 to Wiktor, U.S. Pat. No. 5,292,331 to Boneau, U.S. Pat. No. 5,421,955 to Lau, U.S. Pat. No. 5,776,161 to Globerman, U.S. Pat. No. 5,935,162 to Dang, U.S. Pat. No. 6,090,127 to Globerman, U.S. Pat. No. 6,113,627 to Jang, U.S. Pat. No. 6,663,661 to Boneau, and U.S. Pat. No. 6,730,116 to Wolinsky et al., each of which is incorporated by reference herein in its entirety.

Figure 3:
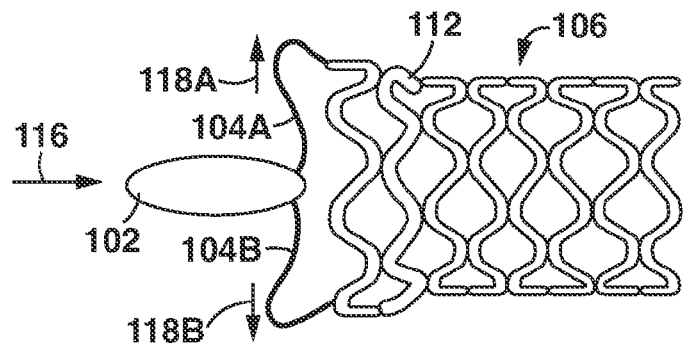
FIGS. 3 and 4 are side views of the implant of FIG. 1, wherein a force is applied to longitudinally relocate the sensor towards the expanded anchor.

After radial expansion of anchor 106 into engagement with the vessel wall, sensor 102 is forced at least part way into lumen 120 of expanded anchor 106 such that the struts 104A, 104B are inverted into an over-center or locked position that holds at least a distal portion of sensor 102 radially centered within a proximal end of lumen 120. More particularly, a force is applied to sensor 102 in the direction of arrow 116 to translate sensor 102 towards the expanded anchor 106 as shown in FIG. 3. The frictional engagement between anchor 106 and the vessel wall is expected to be sufficient to retain anchor 106 in the deployed position while resisting the force applied to translate sensor 102. It should be understood that, without deviating from the teaching of the disclosure, the distal-to-proximal orientation of implant 100 described herein may be reversed such that sensor 102 is initially located distal to anchor 106, in which case the force applied in the direction of arrow 116 is a pulling force rather than a pushing force. The force applied to sensor 102 causes struts 104A, 104B and one or more anchor rings 112 to which struts 104A, 104B are attached to controllably deform, bulging radially outward in the direction of arrows 118A, 118B, as shown in FIG. 3. Struts 104A, 104B thus expand and engage the vessel wall such that, in combination with outwardly deformed anchor ring 112, the resistance of anchor 106 to dislocation by the transformation force is enhanced.

The configuration of implant 100 illustrated in FIG. 3 may be considered to be a "neutral" configuration in that the bulging shape of struts 104A, 104B and ring 112 is inherently unstable. The deformation of struts 104A, 104B and ring 112 in an outward radial direction loads potential energy into the struts and ring 112 and, when released, the struts and ring 112 will tend to seek their least-energy position. That is, if the transformation force were removed at this point during transformation, then implant 100 could either revert itself back to the configuration shown in FIG. 2 or implant 100 could automatically continue the transformation to the final deployed configuration shown in FIG. 5.

Figure 4:
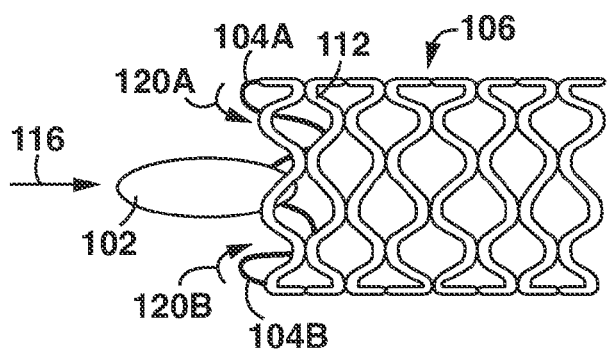
Figure 5:
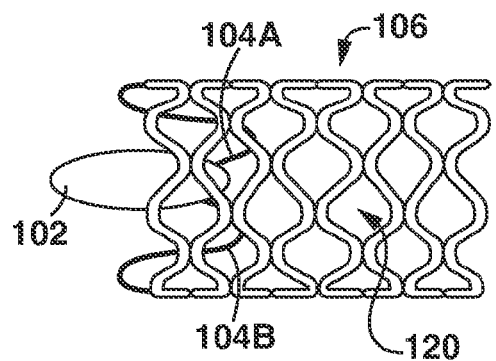
FIG. 5 is a side view of the implant of FIG. 1, wherein the implant is in a final or deployed configuration in which at least a distal portion of the sensor is located and centered within a lumen of the radially expanded anchor.

As the pushing force is continued to be applied in the direction of arrow 116, struts 104A, 104B invert or curve inward in the direction of arrows 120A, 120B, respectively as shown in FIG. 4. In other words, first ends 108A, 108B of struts 104A, 104B longitudinally pass from a proximal side of second ends 110A, 110B to a distal side of second ends 110A, 110B (or vice versa if implant is initially located distal of anchor 106). As struts 104A, 104B invert, the attached end of sensor 102 is longitudinally translated towards and into anchor lumen 120. The potential energy in ring 112 is relieved, and struts 104A, 104B lock into an over-center position shown in FIG. 5 to hold at least a portion of sensor 102 centered within lumen 120 of expanded anchor 106. Struts 104A, 104B are considered to be locked in the over-center position because a substantial force would be required to deform struts 104A, 104B and ring 112 from their least-energy configuration as shown in FIG. 5 to the neutral configuration as described above with respect to FIG. 3. Absent such a substantial force, struts 104A, 104B will remain locked in the over-center position of FIG. 5. By disposing at least a portion of sensor 102 within lumen 120 of anchor 106, the overall length of implant 100 is minimized, which may be particularly advantageous when implanting sensor 102 at an implantation site having a relatively short landing zone within the vessel.

Struts 104A, 104B, as well as anchor 106, may be made from a variety of medical implantable materials, including, but not limited to, nickel-titanium (nitinol), stainless steel, tantalum, nickel, titanium, polymeric materials, nickel-cobalt-chromium-molybdenum "superalloy," combinations of the above, and the like. In one embodiment, struts 104A, 104B are solid wire or wire-like members having an outer diameter that ranges between 0.006 and 0.050 inch and may have a length between 0.50 and 2.00 inches, although the dimensions may be scaled accordingly to match vessels of 4-60 mm in diameter. Struts 104A, 104B may be generally wire-like and have cross-sectional shapes known to those of ordinary skill in the art, including but not limited to circular, elliptical, or rectangular.

In one embodiment, struts 104A, 104B are pre-curved or heat-set in the curved or inverted configuration of FIG. 5 in which struts 104A, 104B curve radially inward from their attachment points on implant 106 towards and within the lumen 120 of anchor 106. The heat-set configurations of struts 104A, 104B are imparted or set into the struts during the manufacturing thereof prior to implantation. Upon application of a sufficient pushing force, struts 104A, 104B transform from the generally straightened configurations of FIG. 1 into their heat-set configurations of FIG. 5, thereby locking into the over-center position to hold at least a distal portion of sensor 102 centered within lumen 120 of expanded anchor 106. By snapping back into predetermined or heat-set configurations, the struts 104A, 104B are even further locked into the final or deployed configuration because the force required to deform struts 104A, 104B would need to overcome both the over-center forces described above as well as the heat-set forces imparted to struts 104A, 104B during the manufacturing thereof.

Figure 6:
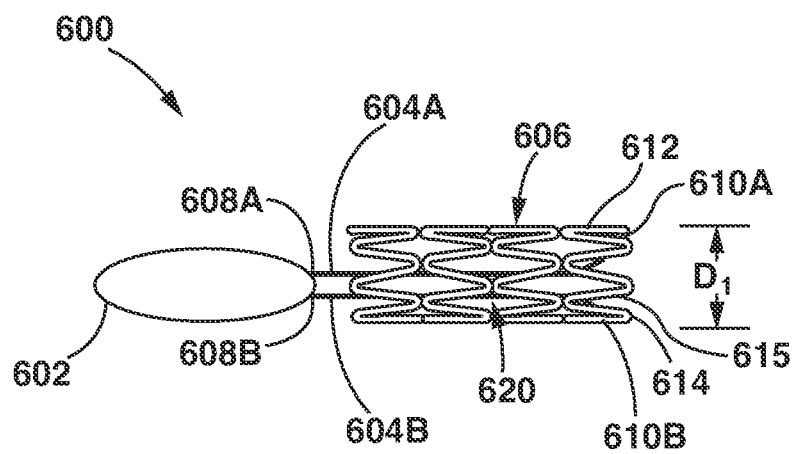
FIG. 6 is a side view of an embodiment of an implant according to another embodiment hereof, wherein the implant is in a compressed or delivery configuration in which a sensor is longitudinally separated from an anchor.
Figure 7:
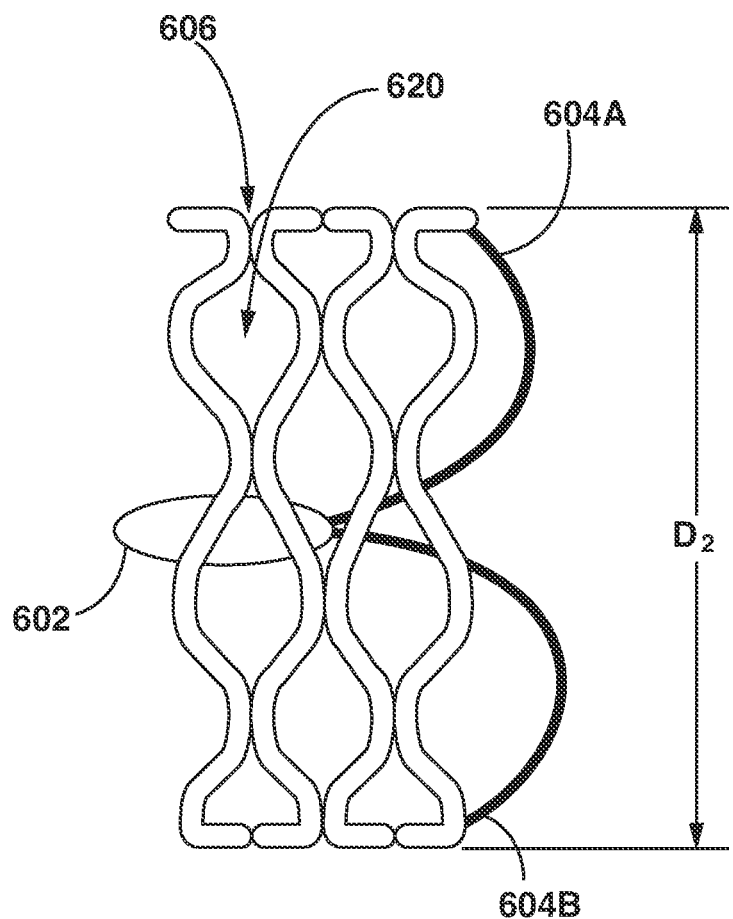
FIG. 7 is a side view of the implant of FIG. 6, wherein the implant is in a final or deployed configuration in which at least a distal portion of the sensor is located and centered within a lumen of the radially expanded anchor.

Turning now to FIGS. 6-7, another embodiment of an implant 600 is shown. FIG. 6 illustrates implant 600 in an initial or delivery configuration in which a sensor 602 is connected and longitudinally separated from a self-expanding anchor 606 by at least two struts 604A, 604B. In one embodiment, a plurality of radially compressible rings 612 is joined in series to form the cylindrical tubular body of anchor 606. Rings 612 may have any suitable configuration, such as a zig-zag or sinusoidal wireform pattern of straight segments 615 with crowns 614 (i.e., alternating crowns facing opposite longitudinal directions) connecting adjacent straight segments 615. FIG. 7 illustrates implant 600 in a final or deployed configuration in which at least a distal portion of sensor 602 is centered within a lumen 620 of expanded anchor 606. Struts 604A, 604B have first ends 608A, 608B, respectively, attached to a distal end of sensor 602 and second ends 610A, 610B, respectively, attached to a distal end of anchor 606. It will be apparent to those of ordinary skill in the art that sensor 602 may alternatively be positioned distal to anchor 606 and first ends 608A, 608B, may be attached to the proximal end of sensor 602 and second ends 610A, 610B may be attached to a proximal end of anchor 606. In addition, it will apparent to those of ordinary skill in the art that other positioning/attachment locations between struts 604A, 604B and anchor 606 are possible. For example, second ends 610A, 610B of struts 604A, 604B may be attached at other longitudinal positions along the length of anchor 606 such as approximately along a proximal portion of anchor 606, a mid-point of anchor 606, or a distal portion of anchor 606.

Struts 604A, 604B are pre-curved or heat-set in a curved configuration as shown in FIG. 7 in which struts 604A, 604B extend distally from their attachment points on the distal end of anchor 606 and then curve radially inward towards and within the lumen 620 of anchor 606. The heat-set configurations of struts 604A, 604B are imparted or set into the struts during the manufacturing thereof prior to implantation. In one embodiment, the heat-set configurations of struts 604A, 604B are generally semi-circular. When implant 600 is loaded into a delivery system, sensor 602 is pulled such that struts 604A, 604B generally straighten out to longitudinally separate sensor 602 from anchor 606 as shown in FIG. 6, thus minimizing the profile of the delivery system. Rather than utilizing an externally applied pulling or pushing force to evert the struts over-center and longitudinally relocate the implant as in the embodiment of FIGS. 1-5, implant 600 utilizes radial expansion of anchor 606 to pull or longitudinally relocate sensor 602 within the expanded anchor 606 during deployment. More particularly, when anchor 606 radially expands within a vessel, the diameter thereof increases from a first diameter $D_1$ of anchor 606 in the compressed or delivery configuration of FIG. 6 to a second diameter $D_2$ of anchor 606 in the deployed or expanded configuration of FIG. 7. In an embodiment, second diameter $D_2$ is between 6 and 10 times the first diameter $D_1$. For example, anchor 606 may have a compressed first diameter $D_1$ approximately equal to 3 mm, which is approximately equal to an outer diameter of sensor 602, and an expanded second diameter $D_2$ between 20 mm and 40 mm. Struts 604A, 604B are pulled longitudinally inward and radially outward as anchor 606 radially expands, until struts 604A, 604B revert or snap back into their heat-set curved configurations. As a result, sensor 602 is longitudinally relocated to a position at least partially within lumen 620 of anchor 606 so that sensor 602 is radially centered inside the lumen of the vessel.

Figure 8:
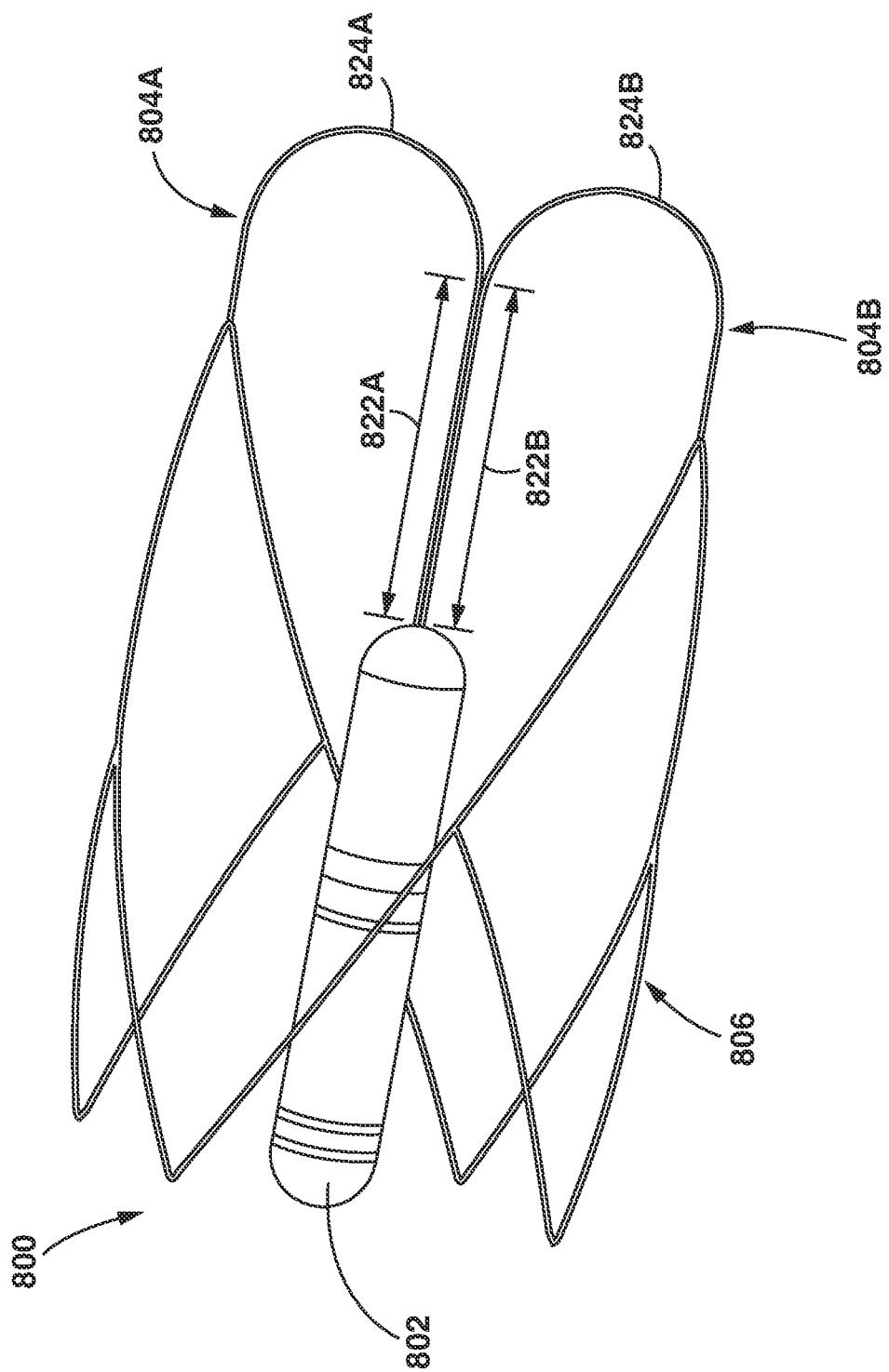
FIG. 8 is a perspective view of an embodiment of an expanded implant.

It will apparent to those of ordinary skill in the art that other preset curved configurations of struts 604A, 604B are possible depending on the relative dimensions, including expanded diameter and length, of anchor 606. For example, FIG. 8 illustrates a perspective view of a radially expanded anchor 806 having sensor 802 at least partially centered therein according to another embodiment hereof. In this embodiment, the expanded diameter of anchor 806 is approximately five (5) times the first compressed diameter. For example, anchor 806 may have a compressed first diameter approximately equal to 3 mm, which is approximately equal to an outer diameter of sensor 802, and an expanded second diameter of approximately 15 mm. Shown in their preset and finally deployed configuration, struts 804A, 804B each include a distal portion 824A, 824B, respectively, that extends distally from their attachment points on the distal end of anchor 806 and then curve radially inward towards and within the lumen of anchor 806 and a generally straight proximal portion 822A, 824B, respectively, that connects to the distal end of sensor 802. In this embodiment, the generally straight proximal portions 824A, 824B provide struts 804A, 804B sufficient length to ensure that sensor 802 is longitudinally separated from anchor 806 when implant 800 is loaded into a delivery catheter. As in the above embodiment of FIGS. 6-7, radial expansion of anchor 806 causes struts 804A, 804B to be pulled longitudinally inward and radial outward during deployment until struts 804A, 804B revert back into their heat-set configurations, thereby longitudinally relocating sensor 802 to a position at least partially within a lumen of expanded anchor 806.

Figure 9:
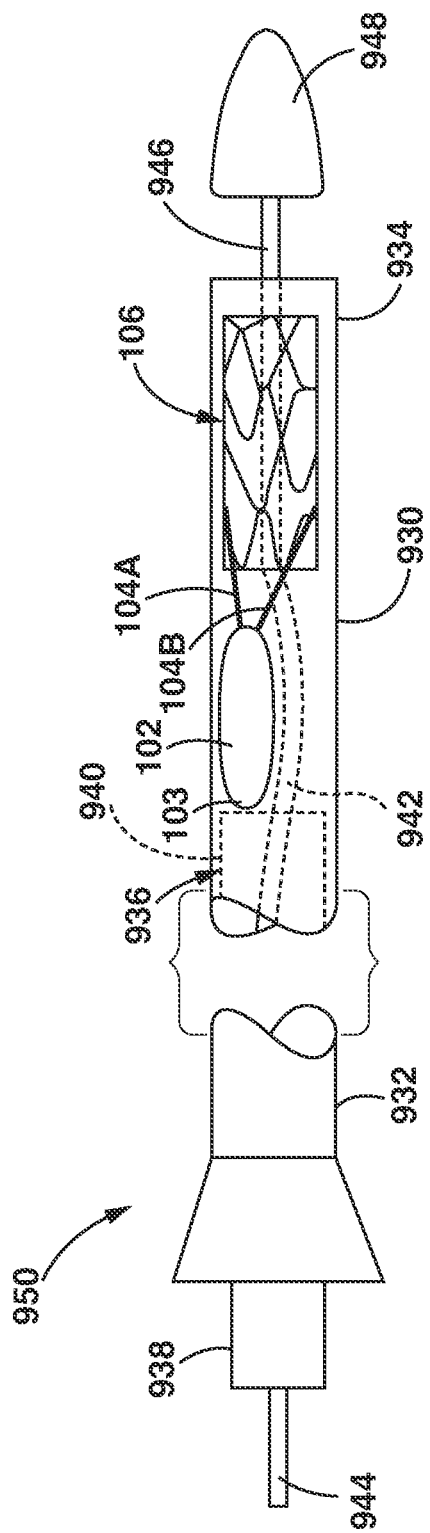
FIG. 9 is a side view of an embodiment of a delivery system.

FIG. 9 illustrates a side view of a system 950 for delivering and deploying implant 100 having a self-expanding anchor 106. Although described with respect to implant 100, delivery system 950 may also be utilized for delivering implants 600, 800 having self-expanding anchors 606, 806, respectively, or any other embodiment described herein that includes a self-expanding anchor. Self-expanding as used herein means that anchor 106 has a mechanical memory to return to an expanded or deployed configuration. Mechanical memory may be imparted to anchor 106 by thermal treatment to achieve a spring temper in stainless steel, for example, or to set a shape memory in a susceptible metal alloy, such as nickel-titanium (nitinol).

The delivery system 950 includes a retractable outer sheath 930 having a proximal end 932 and a distal end 934, an intermediate or pusher tube 936 having a proximal end 938 and a distal end 940, and an inner or core shaft 942 having a proximal end 944 and a distal end 946. Proximal ends 932, 938, and 944 of sheath 930, pusher 936, and shaft 942, respectively, each extend proximally outside of the patient's body such that they may be manipulated by the physician and may include a handle or knob in order to facilitate securing a longitudinal position or sliding movement thereof. Sheath 930, pusher 936, and shaft 942 are concentric in that pusher 936 slidingly extends through a lumen defined by sheath 930 and shaft 942 slidingly extends through a lumen defined by pusher 936. Sheath 930 is an elongated tube that serves to constrain anchor 106 mounted on the inner shaft 942 into the radially compressed delivery configuration described above with respect to FIG. 1 while delivery system 950 is tracked through a patient's vasculature to the deployment site. When sheath 930 is retracted, anchor 106 is released and radially expands as described above with respect to FIG. 2. Pusher 936 is an elongated tube that serves to apply the deployment force (i.e., a pushing or pulling force) to sensor 102 and also serves as a stopper that assists in deployment of self-expanding anchor 106 when outer sheath 930 is retracted. Shaft components 930, 936 may be formed from a flexible polymeric material such as polyethylene terephthalate (PET), nylon, polyethylene, polyethylene block amide copolymer (PEBA), or combinations thereof. Shaft 942 is an elongated solid or tubular component that extends through pusher 936 to a distal tip 948 of delivery system 950. Distal tip 948 is coupled to distal end 946 of shaft 942, and may be tapered and flexible to provide trackability through the vasculature. In an embodiment where shaft 942 is a solid rod, shaft 942 is tracked to the target site with the assistance of tapered distal tip 948. In an embodiment where shaft 942 is a tubular component, shaft 942 may define a guidewire lumen (not shown) for receiving a guidewire (not shown) therethrough. When the guidewire lumen is present, shaft 942 may be advanced over an indwelling guidewire to track the delivery system to the target site.

When loaded into delivery system 950, sensor 102 is connected to but longitudinally separated from anchor 106 via struts 104A, 104B and is positioned between an inner surface of sheath 930 and an outer surface of shaft 942. In the embodiment shown, pusher 936 need not be attached to sensor 102 because pusher 936 can simply provide a pushing deployment force against sensor 102. However, if sensor 102 is initially located distal to anchor 106 such that a pulling deployment force is required, or if the ability to recapture sensor 102 and anchor 106 is desired, a proximal end 103 of sensor 102 may be releasably attached to a distal end 940 of pusher 936. Pusher 936 serves to apply the pushing deployment force onto sensor 102 in order to longitudinally translate sensor 102 to a position within the lumen of anchor 106, as described above with respect to FIGS. 3-5. Once sensor 102 is locked into position as desired, delivery system 950 may be proximally retracted and removed from the patient. If pusher 936 is releasably attached to sensor 102, then pusher 936 is disconnected from sensor 102 prior to removal of delivery system 950. Sensor 102 and pusher 936 may be releasably attached to each other in any suitable manner such as by mating screw threads.

A releasable connection between sensor 102 and pusher 936 may permit recapture and repositioning of the expanded anchor 106. More particularly, initial deployment of anchor 106 may result in a less than optimal positioning or an inoperable positioning of implant 100. A pulling force may be applied to sensor 102 to unlock and straighten struts 104A, 104B. Continued pulling of sensor 102 and/or advancement of sheath 930 radially compresses the proximal end of anchor 106 into sheath 930. Once the proximal end of anchor 106 is collapsed into sheath 930, sheath 930 may be re-advanced over anchor 106 to re-constrain the device therein. Implant 100 may then be repositioned and the deployment process may be repeated at the new implantation site.

In another embodiment, anchor 106 of implant 100 may be balloon-expandable. Anchor 106 may be crimped onto a conventional balloon dilation catheter for delivery to a treatment site where anchor 106 may be expanded by the radial force of the balloon. As the balloon expands, it physically forces anchor 106 to radially expand such that the outside surface of anchor 106 comes into contact with the vessel wall. The balloon is then deflated and collapsed leaving anchor 106 in the expanded or deployed configuration. Conventional balloon catheters that may be modified for use with implant 100 include any type of catheter known in the art, including over-the-wire catheters, rapid-exchange catheters, core wire catheters, and any other appropriate balloon catheters. For example, and not by way of limitation, conventional balloon catheters such as those shown or described in U.S. Pat. Nos. 6,736,827; 6,554,795; 6,500,147; and 5,458,639, which are incorporated by reference herein in their entirety, may be modified for use in conjunction with implant 100 of the present invention. Struts 104A, 104B are separately formed with a predetermined or heat-set configuration as described above, and subsequently connected to the balloon-expandable anchor 106.

Figure 10:
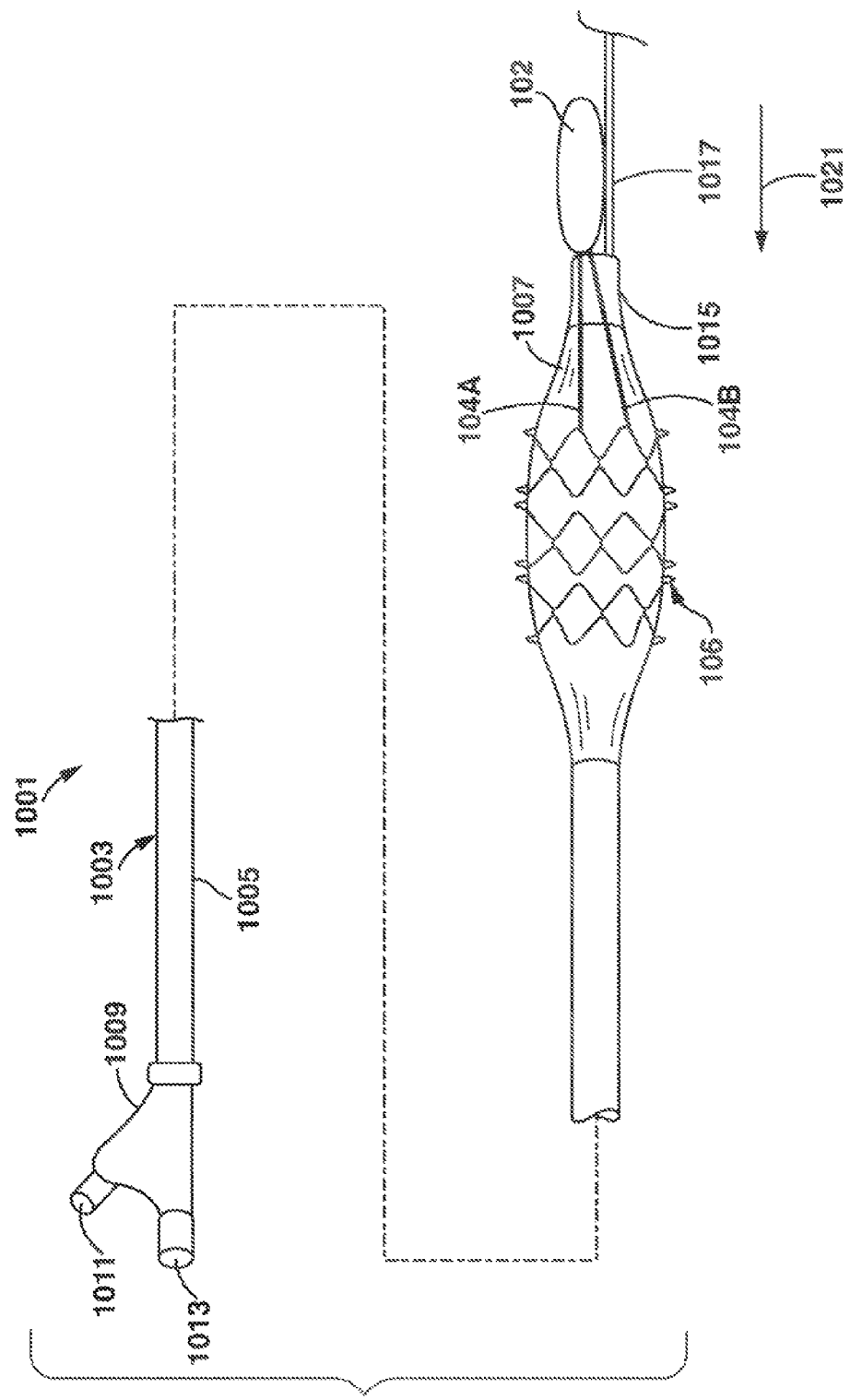
FIG. 10 is a side view of an embodiment of a delivery system.

For example, FIG. 10 is an illustration of a delivery system 1001 for tracking implant 100 having a balloon expandable anchor 106 to a target site in accordance with an embodiment of the present invention. Stent delivery system 1001 includes an over-the-wire catheter 1003 having a catheter shaft 1005 extending from hub 1009 to a distally-mounted balloon 1007. Balloon 1007 is shown in an expanded or inflated configuration in FIG. 10. Inflation port 1011 of hub 1009 fluidly communicates with balloon 1007 via an inflation lumen (not shown) that extends through shaft 1005. In addition, hub 1009 includes a guidewire port 1013 that communicates with a guidewire lumen (not shown) of shaft 1005 for receiving a guidewire 1017 therethrough. Anchor 106 is positioned over balloon 1007 and sensor 102 is releasably coupled to the outer surface of catheter distal tip 1015, with struts 104A, 104B extending between anchor 106 and sensor 102. Sensor 102 may be releasably coupled to catheter tip 1015 in any suitable manner. For example, catheter tip 1015 may have a helical connector (not shown) engaged with sensor 102 such that, after deployment of anchor 106 and deflation of balloon 1007, catheter 1003 can be withdrawn to pull sensor 102 at least partially within anchor 106. Then, catheter shaft 1005 can be rotated to disconnect tip 1015 from sensor 102 and catheter 1003 can then be withdrawn from the patient. If desired, a sheath may be provided to surround implant 100 to facilitate tracking of delivery system 1001 over guidewire 1017 through the vasculature to a site of a stenotic lesion.

Deployment of balloon expandable anchor 106 is accomplished by threading catheter 1003 through the vascular system of the patient until anchor 106 is located at a target location, for example, an implantation site for sensor 102. Once positioned, balloon 1007 may be inflated to expand anchor 106 against the wall of the vessel as is known to one of ordinary skill in the art. With sensor 102 being located distal to anchor 106 as shown in FIG. 10, a pulling force in the direction of directional arrow 1021 is then applied to the proximal end of catheter tip 1015 to longitudinally relocate at least a portion of sensor 102 into a locked and centered position within the lumen of expanded anchor 106.

In alternative balloon-expandable embodiment, sensor 102 may be located proximal to anchor 106 and releasably coupled to catheter shaft 1005. After expanding anchor 106, balloon 1007 must be deflated and a pushing force may be applied to shaft 1005 to longitudinally relocate at least a portion of sensor 102 into a locked and centered position within the lumen of expanded anchor 106. Shaft 1005 is then disengaged from sensor 102, and delivery system 1001 is proximally retracted and removed from the patient.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. An implant centering system comprising:
    a sensor;
    a hollow cylindrical anchor transformable between a radially compressed configuration operable for delivery within a vasculature and a radially expanded configuration operable for lodging against a vessel wall; and
    at least two struts each having a first end connected to the sensor and a second end connected to the anchor;
    wherein the at least two struts are configured such that as the anchor transforms between the radially compressed configuration and the radially expanded configuration the at least two struts longitudinally relocate the sensor between a first position in which the sensor is longitudinally spaced apart from the radially compressed anchor and a second position in which the sensor is at least partially located within a lumen of the radially expanded anchor.

2. The implant centering system of claim 1, wherein the anchor is self-expanding.

3. The implant centering system of claim 1, wherein the anchor is balloon-expandable.

4. The implant centering system of claim 1, wherein the at least two struts are generally straightened when the sensor is in the first position.

5. The implant centering system of claim 1, wherein the at least two struts curve longitudinally inward within the radially expanded anchor when the sensor is in the second position.

6. The implant centering system of claim 5, wherein at least a portion of the at least two struts are heat set in a shape to curve longitudinally within the lumen of the radially expanded anchor.

7. The implant centering system of claim 5, wherein an externally applied force deforms the at least two struts to curve longitudinally inward and lock over-center.

8. The implant centering system of claim 5, wherein radial expansion of the anchor longitudinally relocates the sensor into the second position.

9. The implant centering system of claim 1, wherein each of the at least two struts extend from the sensor to the anchor in the same longitudinal direction.

10. The implant centering system of claim 1, wherein the second end of each of the at least two struts is connected to the anchor an equal longitudinal distance from a first end of the anchor.

11. The implant centering system of claim 5, wherein each of the at least two struts curves more than 90°.

* * * * *